United States Patent [19]

Chang et al.

[11] Patent Number: 4,666,865

[45] Date of Patent: May 19, 1987

[54] IMMUNOASSAY FOR BIOLOGICALLY ACTIVE HUMAN INTERFERON-GAMMA EMPLOYING UNIQUE MONOCLONAL ANTIBODIES

[75] Inventors: Tse W. Chang, Paoli; Patrick C. Kung, Villanova, both of Pa.; Junming Le, New York, N.Y.; Victor Liu, Malvern, Pa.; Jan Vilcek, New York, N.Y.

[73] Assignee: Centocor, Inc., Malvern, Pa.

[21] Appl. No.: 570,353

[22] Filed: Jan. 13, 1984

[51] Int. Cl.$^4$ ............................................. G01N 33/54
[52] U.S. Cl. ..................... 436/518; 436/536; 436/548; 436/531; 436/541; 436/808; 435/68; 435/172.2; 435/240; 935/108; 935/110; 530/351
[58] Field of Search ............... 436/536, 548, 531, 808, 436/541, 518; 260/112 B; 435/68, 172.2, 240; 935/108, 110

[56] References Cited

U.S. PATENT DOCUMENTS

| | | | |
|---|---|---|---|
| 4,376,110 | 3/1983 | David et al. | 436/513 |
| 4,423,147 | 12/1983 | Secher | 436/536 |
| 4,474,892 | 10/1984 | Murad et al. | 436/513 |
| 4,514,507 | 4/1985 | Secher | 436/548 |

FOREIGN PATENT DOCUMENTS 841042 10/1984 European Pat. Off. .

OTHER PUBLICATIONS

Kohler and Milstein, Nature, 256, 495 (1975).
Oleszak et al, Hybridoma, 2(4) pp. 439–449, (1983).
Hochkeppel, H. K. and M. deLey (1982), Nature 296, 258–259.
Rubin, B. Y. et al., (1983) J. Immunol. 130, 1019.
Novick, D. et al., (1983) The Embo J. 2, 1527–1530.

Primary Examiner—Sidney Marantz
Assistant Examiner—Robert Benson
Attorney, Agent, or Firm—Hamilton, Brook, Smith and Reynolds

[57] ABSTRACT

Rapid, sensitive and accurate immunoassays for biologically active natural or recombinant human interferon-gamma (huIFN-gamma) based upon monoclonal antibodies which react specifically with epitopes of the biologically active form of huIFN-gamma are disclosed. The immunoassays include sandwich immunoradiometric assay of the forward, reverse or simultaneous type and competitive binding assay such as radioimmunoassay. The assays are also useful for the detection of macrophage activation factor now believed to be identical to huIFN-gamma. In addition, methods of purification of huIFN-gamma employing the monoclonal antibodies are described.

15 Claims, 12 Drawing Figures

IMMUNOASSAY FOR BIOLOGICALLY ACTIVE HUMAN INTERFERON-GAMMA EMPLOYING UNIQUE MONOCLONAL ANTIBODIES

TECHNICAL FIELD

This invention is in the field of immunochemistry and pertains to methods for detecting, quantifying and purifying biologically active human interferon-gamma (huIFN-gamma) or macrophage activation factor (MAF) employing monoclonal antibodies specific for the active form of human interferongamma.

BACKGROUND ART

Interferon-gamma (IFN-gamma), also called immune interferon, is secreted by T lymphocytes when stimulated by mitogen or antigen. Wheelock, E. F. (1965), Science 149, 310; Johnson, H. M. et al. (1977), Proc. Soc. Exp. Biol. Med. 154, 138; Vilcek, J. et al. (1980) in: Biochemical Characterization of Lymphokines, eds. A. L. DeWeck et al., Academic Press, N.Y., p.323; Ennis, F. A. and Meager, A. (1982) J. Exp. Med. 154, 1279; Chang, T. W. et al. (1982) J. Immunol. 128, 585; O'Malley et al. (1982) J. Immunol. 128, 2522. Like alpha and beta interferons, IFN-gamma mediates the resistance of target cells to viral infection. It also mediates a range of immunoregulatory activities in vivo and in vitro, such as the augmentation of natural killer cell activity and tumoricidal activity. Trinchieri, G. and Santoli, D. (1978) J. Exp. Med. 147, 1314; Hansson et al., (1980) in Natural Cell-Mediated Immunity Against Tumors, ed. R. B. Herberman, Academic Press, N.Y., p. 855; Targan, S. and Stebbing, N. (1982) J. Immunol. 129, 934. In addition, IFN-gamma activates the function of macrophages by triggering proliferation, secretion of soluble factors, and expression of surface Ia and Fc receptor molecules, Steeg, P. S. et al. (1982) J. Immunol. 129, 2402; Basham, T. V. and Merigan, T. C. (1983) J. Immunol. 130, 1492.

Originally, the activation of macrophages was ascribed to a putative lymphokine, termed macrophage activation factor (MAF). However, recently it has become almost certain that IFN-gamma is identical to MAF. Some of the evidence supporting the identity of the two factors includes the following: (1) monoclonal antibodies specific for IFN-gamma neutralize all MAF activity in supernatant of activated T lymphocytes; (2) IFN-gamma and MAF activity are copurified in all isolation procedures; and (3) recombinant E. coli-derived IFN-gamma has potent MAF activity. Roberts, W. K. and Vasil, A. (1982) J. Interferon Res. 4, 519; Schreiber, R. D. et al. (1983) J. Immunol. 131, 826. Nathan, C. F. et al. (1983) J. Exp. Med. 158, 670; Le, J. et al. (1983) J. Immunol. 131, 2821.

As IFN-gamma is such an important T cell factor in host defense and in regulation of immune responses, immunologists have studied how the secretion of IFN-gamma by T lymphocytes is regulated under various conditions in vitro. Also, investigators have sought to determine whether IFN-gamma levels in the circulating blood are measurable, and if so, whether they change during active immune responses or under certain pathological conditions. Using biological assays for human interferon, Ohno and coworkers detected an increase in IFN-gamma levels in serum of patients with Behcet disease, an inflammatory disease of the eye with probable viral or autoimmune etiology. Ohno et al. (1982) Infect. Immun. 36, 202. They also reported that T lymphocytes isolated from these patients in the convalescent stage produce IFN-gamma spontaneously in cell culture. Fujii, N. et al.(1983) J. Immunol. 130, 1683. Later, Cunningham and Merigan found that peripheral blood mononuclear cells isolated from patients within three weeks after the onset of recurrent herpes labialis also secreted IFN-gamma spontaneously into culture medium. Cunningham, A. L. and Merigan, T. C. (1983) J. Immunol. 130, 2397. However, they could not detect IFN-gamma in the serum of these patients.

Functional assays for interferons, generally, are based on the ability of interferons to inhibit lysis of cultured human fibroblasts infected by viruses. See, for example Havell, E. A. and Vilcek, J. (1972) Antimicrob. Agent. Chemother. 2,476. Bioassays of this kind, however, have a number of drawbacks. Many times, they are variable and imprecise because the fibroblasts and viruses used are different. The assays normally take two to three days to run and interpretation of results (the cytopathic changes) is sometimes subjective. Moreover, the assays are not type specific, that is, they do not distinguish between the different types of interferons, IFN-alpha, IFN-beta and IFN-gamma. For these reasons, a rapid, sensitive, objective and type-specific immunochemical assay for human IFN-gamma would be highly desirable.

Monoclonal antibodies have proven useful for the characterization, identification, quantification and purification of various lymphokines. Some monoclonal antibodies to huIFN-gamma have been described in the literature. Hockeppel and De Ley describe a monoclonal antibody of the IgM class which reacts with huIFN-gamma but is unable to neutralize the antiviral activity of the lymphokine. Hockeppel, H. K. and M. De Ley (1982) Nature 296, 258-259. Rubin et al. developed a monoclonal antibody against huIFN-gamma, designated GIF-1, which neutralizes the antiviral activity of natural huIFN-gamma but not recombinant huIFN-gamma, i.e., huIFN-gamma expressed by cells harboring chimeric DNA into which the human gene for IFN-gamma has been inserted by gene-splicing techniques. Rubin, B. Y. et al. (1983) J. Immunol. 130, 1019. Finally, Novick et al. disclose monoclonal antibodies against IFN-gamma useful for affinity purification and immunoassay of huIFN-gamma. Novick, D. et al. (1983) The Embo J. 2, 1527-1530.

DISCLOSURE OF THE INVENTION

This invention pertains to immunochemical assays for biologically active human interferon-gamma (huIFN-gamma) and methods for immunopurification of huIFN-gamma. The assays and immunopurification techniques employ monoclonal anti-huIFN-gamma antibodies which react specifically with the active form of huIFN-gamma. The antibodies do not react with the inactive form of huIFN-gamma. Additionally, the antibodies are interferon-type specific, that is, they react with interferon-gamma but not the alpha and beta types of interferon. Another significant attribute of the antibodies is that they react with both natural huIFN-gamma and recombinant huIFN-gamma.

The immunoassays of this invention include "sandwich" or "two-site" immunoradiometric assays and competitive binding assays such as radioimmunoassays. They provide rapid, highly sensitive, type specific methods of detecting and quantifying biologically active natural or recombinant huIFN-gamma. For instance, a solid-phase forward sandwich immunoradiometric assay is disclosed which may be performed in about 5–6 hours and is capable of detecting levels of huIFN-gamma as low as 0.02 ng/ml.

Because IFN-gamma is apparently identical to MAF, a point explored in more detail infra, the assays serve as a means of detecting and quantifying huIFN-gamma or MAF. As used herein, the term IFN-gamma is meant to include MAF. The antibodies also provide methods of purification of biologically active huIFN-gamma.

BEST MODE OF CARRYING OUT THE INVENTION

Figure 1:
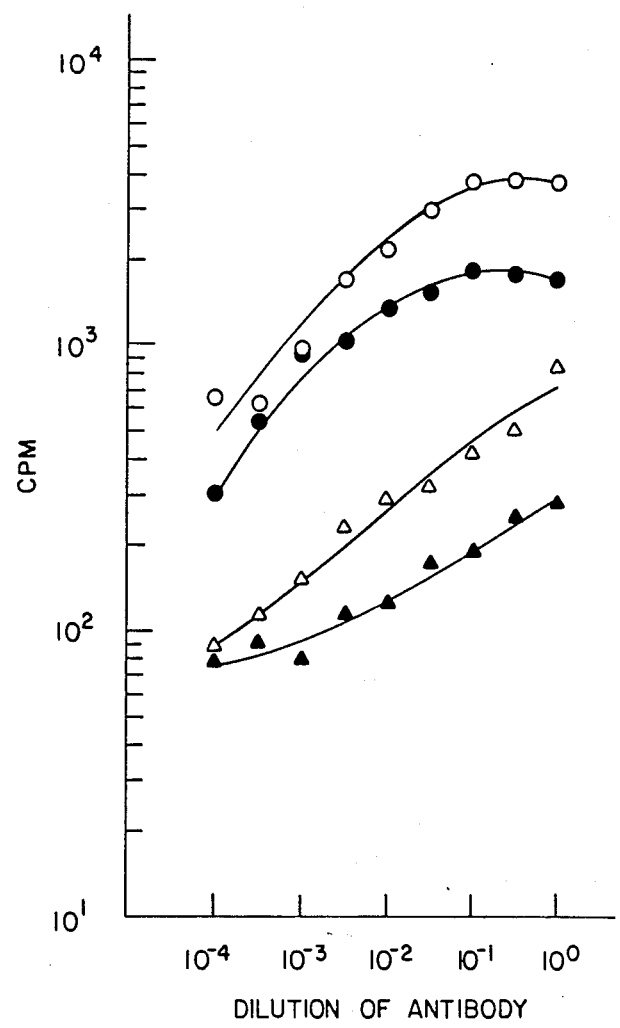
FIG. 1 illustrates the concentration-related binding of monoclonal antibodies B1 and B3 to natural and recombinant huIFN-gamma in a solid phase radioimmunoassay.

To establish groundwork for description of the assays and purification techniques of this invention, the distinctive characteristics of the monoclonal antibodies of this invention are described.

Monoclonal anti-huIFN-gamma antibodies of this invention specifically react with epitopes of huIFN-gamma associated with the biologically active configuration of the lymphokine. Two monoclonal antibodies specific for distinct epitopes of biologically active huIFN-gamma have been prepared. These antibodies are designated B1 and B3. The antibodies have been deposited at the American Type Culture Collection (ATCC) in Rockville, Md. and have been assigned the following ATCC accession numbers:

| Antibody | ATCC Accession No. |
| --- | --- |
| B1 | 40096 |
| B3 | 40097. |

Both antibody B1 and B3 antibody exhibit dose-related binding to purified natural huIFN-gamma and recombinant E. coli-derived huIFN-gamma in direct binding assays and in immunoprecipitation assays. The antibodies are type specific; neither antibody exhibits reactivity toward any other types of interferon. Although each antibody reacts with the active form of the huIFN-gamma, the B3 antibody neutralizes the antiviral activity of the molecule. It neutralizes the anti-viral activity of both natural and E. coli derived recombinant huIFN-gamma. The monoclonal antibody B1 does not neutralize the anti-viral activity of either natural or recombinant huIFN-gamma. Additionally, the B1 and B3 antibodies do not compete in binding to huIFN-gamma. These results indicates that the two antibodies bind to different epitopes on the molecule.

In addition to neutralizing the antiviral activity of huIFN-gamma, the monoclonal antibody B3 exhibits several other significant properties. The B3 antibody abolishes the ability of natural huIFN-gamma and recombinant huIFN-gamma to augment monocyte cytotoxicity for tumor cells. The B3 antibody also abolishes induction of monocyte cytotoxicity by mitogen-induced lymphocyte cultures. Thus, the B3 antibody neutralizes the MAF-like activity of huIFN-gamma. This supports the belief that huIFN-gamma and MAF are the same entity. Additionally, when the anti-viral activity of supernatants of mitogen-activated T lymphocytes is neutralized with B3 antibody, MAF activity is coincidentally abrogated in these preparations. That both activities are abolished by the B3 antibody indicates that MAF activity in these preparations is due entirely to IFN-gamma.

The capability of the B3 antibody to neutralize both natural huIFN-gamma and E. coli derived huIFN-gamma is one characteristic which sets it apart from the monoclonal anti-huIFN-gamma antibody GIF-1 described by Rubin et al. The GIF-1 antibody neutralizes the anti-viral activity of natural huIFN-gamma, but it does not neutralize the antiviral activity of E. coli derived recombinant huIFN-gamma. See Rubin, B. Y. et al. (1983) J. Immunol. 13, 1019. Thus, the B3 antibody recognizes an entirely different epitope on the IFN-gamma molecule than does the GIF-1 antibody. The epitope recognized by the B3 antibody is common to both natural and recombinant huIFN-gamma, while that recognized by GIF-1 is specific to natural huIFN-gamma.

Evidence that the B3 antibody reacts only with active huIFN-gamma derives from several sources. In a solid phase radioimmunoassay, the B3 antibody binds to insolubilized IFN-gamma but not to huIFN-gamma inactivated by acid (pH 2) and heat treatment. In addition, the B3 antibody does not bind to sodium dodecyl sulfate $NaDodSO_4$ treated natural or recombinant huIFN-gamma, apparently owing to the denaturation of IFN-gamma by $NaDodSO_4$.

As pointed out, the B1 antibody binds huIFN-gamma in direct binding assays and immunoprecipitates huIFN-gamma, but it does not neutralize the anti-viral activity of either natural or recombinant huIFN-gamma. This implies that the epitope with which the B1 antibody reacts is not associated with the "active site" of the molecule and that it is different from the epitopes recognized by the B3 and the GIF-1 antibodies. Though not associated with the active site of the molecule, the epitope recognized by the B1 antibody is nevertheless distinctive to the biologically active form of huIFN-gamma. Like the B3 antibody, the B1 antibody does not bind to IFN-gamma exposed to NaDodSO$_4$. And, as detailed below, the B1 antibody binds only the active form of the molecule when used in affinity chromatography.

Affinity chromatography on columns formed of monoclonal antibodies have been used for purification of human leukocyte (IFN-alpha) and human fibroblast (IFN-beta) interferon with recoveries of about 50-60% of IFN activity reported. See Novick, D. et al. (1982) *J. Immunol.* 129, 2244; Novick D. et al. (1983) *J. Gen. Virol.* 64, 905. The monoclonal antibodies of this invention, because they specifically bind the biologically active form of huIFN-gamma, may be used for affinity purification of the active molecule.

Immunopurification of huIFN-gamma may be performed according to the following procedure. A monoclonal antibody which binds biologically active huIFN-gamma is immobilized by affixing it to a solid phase to form an immunoadsorbent which specifically adsorbs biologically active huIFN-gamma. A liquid sample from which biologically active huIFN-gamma is to be purified is contacted with the immunoadsorbent under conditions which allow the IFN-gamma in the liquid to be adsorbed by the immunoadsorbent. The immunoadsorbent and the liquid are then separated. Usually, the immunoadsorbent is washed, and then, the IFN-gamma is recovered from the immunoadsorbent.

In conventional affinity chromatography, the immunoadsorbent usually comprises antibody-conjugated particles which are packed into a column. This is the convenient embodiment for interferon affinity purification. Anti-huIFN-gamma antibody-conjugated particles, preferably beads, are packed into a column and the IFN-gamma-containing liquid is passed through the column. The IFN-gamma is retained because of the binding affinity of the immunoadsorbent for the lymphokine. After washing, the IFN-gamma is recovered, most often by elution with an eluant which causes the bound huIFN-gamma to dissociate from the immunoadsorbent. The eluant should yield high recovery of huIFN-gamma, that is, the eluant should cause complete dissociation of the huIFN-gamma from the immunoadsorbent without causing any significant loss of biological activity.

The B1 antibody is particularly suitable for affinity chromatography. When a highly purified preparation of radiolabeled huIFN-gamma is loaded onto an affinity column prepared with the B1 antibody-coated Sepharose beads, only a small fraction of the total radioactivity binds to the affinity column, and the bulk of this bound huIFN-gamma is eluted in biologically active form. The unbound radioactivity lacks IFN-gamma activity yet exhibits an electrophoretic profile similar to that of the eluted fraction which contains all activity, indicating that the unbound protein is very likely inactive huIFN-gamma. Analysis of the IFN-gamma eluted from the column indicates that both of the known subspecies of IFN-gamma, the 25,000 and 20,000 molecular weight subunits, and the presumed dimer of 45,000 molecular weight, are adsorbed by the B1 antibody affinity column.

Recovery of up to 81% of the huIFN-gamma activity applied to the column has been obtained with B1 antibody columns but only when the IFN-gamma is eluted into serum containing buffered tissue culture medium. Those skilled in the art may improve the technique by modifying the elution conditions by routine experimentation.

The monoclonal anti-human IFN-gamma antibodies which exhibit the characteristics set forth above are produced by antibody-producing cell lines. The antibody-producing cell lines include hybrid cell lines commonly known as hybridomas. The hybridomas are formed from the fusion of an anti-human IFN-gamma antibody-producing cell and an immortalizing cell line, that is, a cell line which imparts long term tissue culture stability to the resulting hybrid cell. In the formation of the hybrid cell lines, the first fusion partner—the anti-human IFN-gamma antibody-producing cell—can be a B lymphocyte obtained from the spleen, peripheral blood, lymph nodes or other lymphoid tissue of an animal immunized against huIFN-gamma. The second fusion partner—the immortalizing cell—can be a lymphoblastoid or plasmacytoma cell (myeloma cell). Alternatively, the immortalizing cell itself can be a hybrid cell such as a non-antibody-secreting hybridoma. Shulman, M. et al. (1978) *Nature* 276, 269.

The B1 and B3 monoclonal antibodies are produced by murine hybridomas formed by fusion of a mouse hybridoma which does not secrete antibody and murine spleen cells which secrete antibodies obtained from mice immunized against human IFN-gamma.

Purified human IFN-gamma for immunization may be isolated from culture media of activated human lymphocytes. A preferred method for isolation and purification of human IFN-gamma for immunization is the method described by Yip, Y. K. et al. (1982) *Proc. Natl. Acad. Sci. USA* 79, 1820; and Anderson, P. et al. (1983) *J. Biol. Chem.* 258, 6479. Purification of IFN-gamma increases the likelihood of obtaining anti-huIFN-gamma antibody-producing spleen cells.

A variety of different immunization protocols can be used to immunize the mice. In general the mice are administered a primary injection of huIFN-gamma followed by a number of boosting injections of the lymphokine. During or after the immunization procedure, serum of the mice may be screened to identify those mice in which a substantial immune response to the IFN-gamma has been evoked. From selected mice, the spleen cells are obtained and fusions are performed. Suitable fusion techniques are the Sendai virus technique, Kohler, G. and Milstein, C. (1975) *Nature* 256, 495, or the polyethylene glycol method, Kennet, R. H. in "Monoclonal Antibodies, Hybridomas—A New Dimension in Biological Analyses", ed. R. H. Kennet, T. J. McKearn and K. B. Bechtol, Plenum Press, N.Y., 1980. Also, electrofusing techniques may be employed. Zimmerman, U. and Vienken, J. (1982) *J. Membrane Biol.* 67, 165.

The hybridomas are then screened for production of anti-huIFN-gamma antibody. A suitable screening technique is a solid phase radioimmunoassay. A solid phase immunoadsorbent is prepared by coupling huIFN-gamma to an insoluble matrix. The immunoadsorbent is brought into contact with culture supernatants of hybridomas. After a period of incubation, the solid phase is separated from the supernatants, then contacted with a labeled antibody against murine immunoglobulin. Label associated with the immunoadsorbent indicates the presence of hybridoma products reactive with IFN-gamma. The hybridoma products are then examined for their ability to react with natural and recombinant huIFN-gamma, and active and inactive forms of the molecule.

The monoclonal anti-huIFN-gamma antibodies are produced in large quantities by injecting anti-huIFN-gamma producing hybridoma cells into the peritoneal cavity of mice, and after an appropriate time, harvesting ascites fluid from the mice which yields a very high titer of homogenous antibody and isolating the monoclonal antibodies therefrom. Alternatively, the antibodies can be produced by culturing anti-huIFN-gamma producing cells in vitro and isolating secreted monoclonal anti-huIFN-gamma antibodies from the cell culture medium.

Because the antibodies of this invention discriminate between the active and inactive forms of huIFN-gamma, they permit immunochemical assay of biologically active huIFN-gamma. A particularly preferred type of immunochemical assay is a sandwich immunoradiometric assay (IRMA) in which antigen is measured directly by reacting it with an excess of labeled antibody. In such assays, before the antigen is reacted with labeled antibody, it is insolubilized on an immunoadsorbent which specifically binds the antigen. The immunoadsorbent is formed by affixing an antibody specific for biologically active huIFN-gamma. In sandwich assays for an antigen which is monomeric, two antibodies which recognize distinct epitopes on the antigen are required so that there is no competition for binding to antigen. One is used to form the immunoadsorbent; the other is used as the labeled tracer. In assays for dimeric or polymeric antigens, the same antibody can be used to form the immunoadsorbent as as the labeled tracer.

Sandwich IRMA's may be performed in forward, reverse or simultaneous mode.

In a forward sandwich assay for huIFN-gamma, a monoclonal antibody directed against an epitope of biologically active huIFN-gamma is affixed to a solid phase to form an immunoadsorbent specific for biologically active huIFN-gamma. A liquid sample containing huIFN-gamma is incubated with the immunoadsorbent. Incubation is maintained for a sufficient period of time to allow the huIFN-gamma in the liquid sample to bind the immobilized antibody on the immunoadsorbent. After this first incubation, the solid phase immunoadsorbent is separated from the incubation mixture. The immunoadsorbent may be washed to remove unbound huIFN-gamma and interfering substances, such as non-specific binding proteins, which may also be present in the liquid sample. The immunoadsorbent containing huIFN-gamma bound to immobilized antibody is subsequently incubated with labeled antibody specific for biologically active huIFN-gamma. The antibody may be the same antibody as that immobilized to form the immunoadsorbent, or it may be an antibody specific for a different epitope of biologically active huIFN-gamma. Again, the incubation is carried out for a period of time and under conditions sufficient to ensure binding of the labeled antibody to IFN-gamma. After the second incubation, another wash may be performed to remove unbound labeled antibody from the solid phase immunoadsorbent. The labeled antibody bound to the solid phase immunoadsorbent is then measured, and the amount of labeled antibody detected serves as a direct measure of the amount of biologically active huIFN-gamma present in the liquid sample.

The B1 and B3 monoclonal antibodies provide the basis for an extremely sensitive forward sandwich IRMA for huIFN-gamma. In preferred configuration, the B1 antibody is used to form the immunoadsorbent and the B3 antibody serves as the labeled antibody, and the assay is performed as outlined. With these two antibodies, the assay is specific for biologically active huIFN-gamma and highly sensitive; levels of huIFN-gamma in serum or tissue culture fluid at limiting concentrations of 0.02 ng/ml have been detected. This represents at least a forty-fold increase in sensitivity over existing bioassays for IFN-gamma which have only detected at levels of 1 ng–10 ng/ml.

Recently Novick et al. described an IRMA employing mouse monoclonal antibodies against huIFN-gamma. See Novick, D. et al. (1983) *The EMBO J.* 2, 1527. The reported sensitivity of this assay was 4 ng/ml. By comparison, the assay of this invention is about two hundred times more sensitive. Further there is no indication that the assay of Novick et al. is specific for biologically active huIFN-gamma.

The forward sandwich IRMA may also be run in the opposite configuration, that is, the B3 antibody may be used to construct the solid phase immunoadsorbent and the B1 antibody used as the soluble labeled antibody. However, in this configuration a decrease in sensitivity is observed, probably because the B3 antibody has a higher affinity for huIFN-gamma than the B1 antibody.

The forward sandwich IRMA can also be constructed with one of the antibodies, e.g. either the B1 or B3. In this case, the antibody immobilized to form the immunoadsorbent and the labeled antibody are the same. A sandwich IRMA of this configuration may be used to assay dimeric or polymeric forms of biologically active huIFN-gamma.

The sandwich IRMA may also be performed in reverse and simultaneous modes. In reverse mode, an incubation mixture is formed of the liquid sample to be tested and a soluble labeled antibody directed against an epitope of biologically active huIFN-gamma (e.g. labeled B3 antibody). The mixture is incubated, then contacted with a solid phase immunoadsorbent containing a monoclonal antibody directed against the same (e.g. the B3 antibody) or a different epitope (e.g. the B1 antibody) of biologically active huIFN-gamma. After another incubation, the immunoadsorbent is separated from the mixture and the label bound to the immunoadsorbent is taken as an indication of the amount of huIFN-gamma in the liquid sample.

In the simultaneous mode, an incubation mixture is formed of the liquid sample, the labeled anti-huIFN-gamma antibody and the solid phase immunoadsorbent. When antibodies which react with different epitopes are employed, they do not compete for binding. After appropriate incubation, the solid phase immunoadsorbent is separated from the mixture and the label associated with the immunoadsorbent is measured to give an indication of the amount of biologically active hu-IFN-gamma in the liquid sample.

For each incubation step in the various formats of the assays, the time and conditions of incubation are selected to ensure maximal binding huIFN-gamma to the immobilized antibody and to labeled antibody. In the forward IRMA, where two incubation steps are required, the solid phase immunoadsorbent containing immobilized anti-huIFN-gamma antibody is incubated with the liquid sample for about two hours at room temperature to obtain maximal binding. The optimal duration of the subsequent incubation with labeled antibody is about three hours at room temperature. The entire assay may be run in about 5-6 hours. Thus, besides being the most sensitive assay for huIFN-gamma heretofore described, the assay is the most rapid. The parameters which yield maximal binding of huIFN-gamma may be established for other formats of the IRMA by no more than routine experimentation.

In addition to the IRMA's described herein, the immunoassays of this invention include competitive binding assays such as radioimmunoassay (RIA). A preferred type of RIA is a solid phase RIA.

A solid phase immunoadsorbent is prepared as described for the IRMA.

The immunoadsorbent is then incubated with the liquid sample and a known amount of labeled IFN-gamma for a period of time and under conditions which permit binding of the IFN-gamma to the immunoadsorbent. The immunoadsorbent is separated from the liquid sample and the amount of label associated therewith is assessed. By reference to a preestablished inhibition curve defining the relationship between labeled huIFN-gamma associated with the immunoadsorbent and the amount of unlabeled huIFN-gamma in the liquid sample, the amount of huIFN-gamma in the liquid sample is determined.

In the various solid phase assays of this invention, the immunoadsorbent is separated from incubation mixtures containing the liquid sample, the labeled antibody or both. Separation can be accomplished by any conventional separation technique such as sedimentation or centrifugation. Preferably, though not necessarily, the immunoadsorbent is washed prior to contacting it, when required, with a second incubation medium and prior to measuring the amount of label associated with the immunoadsorbent. The washing removes nonspecific interfering substances or excess labeled antibody which may affect the accuracy and sensitivity of the assay.

The immunoassays of this invention are used to detect and quantify huIFN-gamma in a liquid sample. Liquid samples include essentially all biological fluids such as blood, or components of blood such as plasma or serum and urine, lymph, etc. Also, the liquid sample may be a sample of a liquid medium in which lymphocytes or other mammalian cells have been cultured. They may also be extracts or supernatants of microbial cultures.

As noted, the assays can be used to detect recombinant huIFN-gamma produced by genetically altered cells. Recombinant huIFN-gamma detectible by the assays includes huIFN-gamma expressed by genetically engineered microorganisms such $E.\ coli$, or genetically engineered yeast or mammalian cells.

In the solid phase IRMA's and RIA's of this invention the monoclonal antibodies reactive with biologically active huIFN-gamma are immobilized by affixing them to a solid phase to create an immunoadsorbent. Many types of solid-phases may be employed. Well-known solid phases include beads formed from glass, polystyrene, polypropylene, dextran, and other materials; tubes formed from or coated with such materials, etc. The antibody can be either covalently or noncovalently bound to the solid-phase by techniques such as covalent bonding via an amide or ester linkage or adsorption. Those skilled in the art will know many other suitable solid-phases and methods for immobilizing antibodies thereon, or will be able to ascertain such using no more than routine experimentation.

In each of the IRMA's, a monoclonal anti-huIFN-gamma antibody directed against an epitope of biologically active huIFN-gamma is also used as the labeled antibody (tracer). Such antibodies can be labeled with a radioactive material, such as $^{125}I$; labeled with an optical label, such as a fluorescent material; labeled with an enzyme; or labeled by some other technique.

To determine the amount of huIFN-gamma in the liquid sample, either the amount of label associated with the immunoadsorbent or the amount of unbound labeled antibody, that is, labeled antibody which remains in soluble form, is measured. Generally, it is preferable to measure the label bound to the immunoadsorbent because at very low concentrations of antigen, only small amounts of labeled antibody bind the immunoadsorbent. Thus, for accuracy the label associated with the immunoadsorbent should be measured directly. The label may be detected by a gamma counter, for example, if the label is a radioactive gamma emitter, or by a fluorimeter, for example, if the label is a fluorescent material. In the case of an enzyme label, detection may be done by colorimetric methods employing a competing substrate for the enzyme.

The measured amount of label detected is then compared to a pre-established quantitative relationship between the amount of label and the amount of biologically active hu-IFN-gamma. The quantitative relationship can be determined by performing the IRMA with standards—liquid samples containing known amounts of biologically active huIFN-gamma. For several samples containing different amounts of huIFN-gamma, the assay is conducted and the amount of label either bound or unbound to the immunoadsorbent is determined; a curve is constructed defining the quantitative relationship between the amount of label and the amount of huIFN-gamma. By reference to the curve, the amount of huIFN-gamma in a liquid sample containing an unknown amount of huIFN-gamma can be determined from the amount of label detected.

The reagents for performing the assays of this invention may be assembled in assay kits. For instance a kit for performing an IRMA for huIFN-gamma would comprise a solid phase immunoadsorbent containing an antibody specific for one epitope of biologically active huIFN-gamma, a labeled monoclonal antibody specific for a different epitope of biologically active IFN-gamma and, optionally, an huIFN-gamma standard. The B1 and B3 monoclonal antibodies are suitable for kits because reagents formed with the B1 and B3 monoclonal are stable over a significant period of time when stored. For example B1 antibody-coated polystyrene beads (the immunoadsorbent) and $^{125}I$-radiolabeled B3 antibody have retained complete activity for at least 8 weeks when stored at 4° C. HuIFN-gamma standards are not stable at elevated temperatures.

The invention is illustrated further by the following examples.

EXAMPLES

Example 1

Preparation and Characterization of Monoclonal Anti-IFN-gamma Antibody B1 and B3

Immunization and fusion. Ten week-old female BALB/c mice were obtained from Charles River Breeding Labs, Inc., Wilmington, Mass. Human IFN-gamma was prepared from the cultures of lymphocyte-rich plateletpheresis residues induced with phytohemagglutinin A (PHA) and 12-0-tetradecanoylphorbol-13-acetate (TPA). The huIFN-gamma was purified by a four step protocol (See Yip, Y. K. et al. (1982) *Proc. Natl. Acad. Sci. USA* 79, 1820) to a specific activity of $3 \times 10^5$ units/mg of protein, and then used for immunization. Ten thousand units of IFN-gamma emulsified with an equal volume of complete Freund adjuvant (Difco Laboratories, Detroit, Mich.) in 0.6 ml was injected subcutaneously into the back and footpads of a mouse. Three consecutive injections of $1 \times 10^4$ units of IFN-gamma without adjuvant were given intraperitoneally to the same mouse at 1 week intervals starting one week after the first immunization. The mouse was boosted intraperitoneally 7 weeks later with $2.4 \times 10^4$ units of IFN-gamma. Four days after the last injection, when the antibody titer of the serum was 320 neutralizing units/ml, the mouse was sacrificed. The spleen cells were fused with non-secreting hybridoma SP2/0 (See Shulman et al. (1978) *Nature* 276, 269) at a 5:1 ratio of spleen cells to SP2/0 cells with 0.2 ml 30% PEG 1,000 (J.T. Baker Chemical Co., Phillipsburg, N.J.). The fused cells were distributed in 0.2 ml aliquots into 96-well culture plates (Corning Glass Works, Corning, N.Y.) at a concentration of $2 \times 10^4$ SP2/0 cells per well in the presence of $5 \times 10^4$ spleen cells of a normal BALB/c mouse as feeder cells. Positive wells were subcloned at limiting dilution (1 cell/ml in 0.2 ml culture) on mouse feeder cells. The growth medium consisted of RPMI-1640 medium, 10% heat-inactivated fetal bovine serum (FBS, Gibco Laboratories, Grand Island, N.Y.), 0.1 mM MEM nonessential amino acids, 1 mM sodium pyruvate, 2 mM L-glutamine, 100 U/ml penicillin and 100 ug/ml streptomycin (Gibco Laboratories, Grand Island, N.Y.). During the first 4 weeks after fusion cells were cultured in growth medium containing $1 \times 10^{-4}$M hypoxanthine, $4 \times 10^{-7}$M aminopterin and $1.6 \times 10^{-5}$M thymidine (Medium Laboratory, Sloan-Kettering Institute for Cancer Research, N.Y.).

Solid phase radioimmunoassays. A solid phase radioimmunoassay (SPRIA) using vinyl assay strips (Costar, Cambridge, Mass.) was developed for screening monoclonal antibodies. Human IFN-gamma, purified by a four-step protocol (See Anderson et al., supra), was diluted to 5,000 units/ml with 0.05 M bicarbonate-carbonate buffer (BCB), pH 9.6, and 100 ul of the solution was added to each well. In some experiments *E. coli*-derived human recombinant IFN-gamma (rIFN-gamma) [See Gray et al. (1982) *Nature* 295, 503] with a specific activity of approximately $10^6$ units/mg (generously provided by Genentech Inc., South San Francisco, Calif.) was also used at the same concentration. After incubation at 37° C. for 2 hours, the strips were briefly washed with BCB, then sealed with 1% bovine serum albumin (BSA, RIA grade, Sigma Chemical Co., St. Louis, Miss.) in BCB, 200 ul per well at 37° C. for 1 hour to prevent nonspecific binding. The strips were then washed 3 times with phosphate-buffered saline containing 0.05% Tween 20 (PBS-Tween), and 70 ul of the culture supernatants to be screened were added to each well. In control wells, 70 ul of BCB or medium were added. The strips were incubated for 2 hours at 37° C., and washed 3 times with PBS-Tween. Thereafter, approximately 50,000 counts per min(cpm) of $^{125}$I-labeled F(ab')$_2$ fragment of sheep antibody against mouse immunoglobulins (Ig) (Amersham International, UK) in 50 ul of 1% BSA in PBS-Tween was added to each well, and the strips were incubated for an additional 2 hours at 37° C. The wells were washed 4 times with PBS-Tween, cut and counted individually in a gamma counter.

A solid phase radioimmunoassay was used to assess the reactivity of antibody with active and inactive forms of huIFN-gamma. Approximately 500 units of highly purified huIFN-gamma in 0.1 ml PBS, or the same amounts of IFN-gamma inactivated by pH 2 and heat treatment, were added to each vinyl well. After incubation for 2 hours, the wells were briefly washed, and then sealed with 1% BSA for 1 hour. The wells were then washed 3 times with PBS-Tween, and approximately 40,000 cpm of purified $^{125}$I-labeled B3 antibody were added to each well. The wells were incubated for an additional 2 hours and then washed 4 times with PBS-Tween, cut and counted.

Immunoprecipitation assay. Human natural IFN-gamma preparations purified by a three-step (See Yip, Y. K. et al. (1982) *Proc. Natl. Acad. Sci.* 79, 1820) or four-step protocol, and recombinant IFN-gamma, were iodinated with $^{125}$I-Bolton-Hunter reagent as described by Anderson et al., supra. Approximately 3,000 cpm of $^{125}$I-labeled IFN-gamma in 50 ul of growth medium was incubated with 50 ul of hybridoma supernatant, or medium as blank control, in a microcentrifuge tube, for 90 minutes at 37° C. Fifty ul of rabbit antibody against mouse Ig (Cappel Laboratory, Cochranville, Penn.), diluted 1:50 with PBS, was then added and incubated for 30 minutes at 37° C. Immunoprecipitation was carried out by adding 50 ul of Pansorbin (10% *Staphylococcus aureus* cells, Calbiochem-Behring Corp., La Jolla, Calif.), prewashed sequentially with 20 mM Tris HCl/0.15 M NaCl, pH 7.4, plus 0.5% nonidet p40 (NP40), and with the same buffered solution plus 0.05% NP40. The mixtures were incubated for 15 minutes at 37° C., then centrifuged at $12,800 \times g$ for 1 minute. The pellets were washed once with PBS and then counted in a gamma counter.

IFN assay and neutralization. The antiviral activity of human IFN-gamma was assayed by inhibition of the cytopathic effect of encephalomyocarditis (EMC) virus in human diploid FS-4 fibroblasts in microtiter plates (Havell, E. A. and Vilcek, J. (1972) *Antimicrob. Agents Chemother.* 2, 476). Titers of IFN-gamma are reported in laboratory units without correction (Yip, Y. K. et al. (1981) *Infect. Immun.* 34, 131). Purified human IFN-alpha (Key Interferon, Tampa, Fla.) and IFN-beta (Cytotech SA, Martigny, Switzerland) were assayed by a similar method using FS-4 fibroblasts and EMC virus, and FS-4 cells and vesicular stomatitis virus, respectively.

For neutralization assay, samples were incubated with monoclonal antibody in culture supernatant or ascites form for 1 hour at 37° C., and residual IFN activities were determined. To titrate the neutralizing activity of antibodies, serial dilutions of antibody preparations (100 ul) were mixed with IFN-gamma (30 U/ml in 50 ul) and incubated in microtiter plates for 1 hour at 37° C. FS-4 cells were then added to the wells. The cultures were challenged with EMC virus after overnight incubation. One neutralizing unit is defined as the reciprocal of antibody dilution required to neutralize the antiviral action of IFN-gamma, determined by reversal of the inhibitory action on viral cytopathic effect.

Microcytotoxicity assay. Peripheral blood mononuclear cells (PBM) of normal donors were isolated by fractionation of buffy coat preparations on a Ficoll-Paque (Pharmacia Fine Chemicals, Piscataway, N.J.) gradient, and suspended in RPMI-1640 medium supplemented with 10% FBS, 2 mM L-glutamine, 20 mM HEPES, 100 U/ml penicillin, 100 ug/ml streptomycin and 50 ug/ml gentamicin (Sigma) (hereafter, complete medium). PBM at $3 \times 10^6$ cells per ml were incubated for 2 hours at 37° C. in tissue culture flasks coated with FBS for 2 hours at 4° C. Adherent monocytes were gently washed twice with complete medium and then detached by treatment with PBS containing 0.2% EDTA and 5% FBS for 30 minutes at 4° C. The purity of monocytes was greater than 90% as determined by γ-naphthyl butyrate esterase staining. Target tumor cell line HT-29, a human adenocarcinoma line obtained from Dr. J. Fogh, Sloan-Kettering Institute for Cancer Research, was cultured as a monolayer. HT-29 cells were labeled with 5 uCi $^{125}$iododeoxyuridine ($^{125}$IUdR, New England Nuclear, Boston, Mass.) in a 25 cm$^2$ tissue culture flask (Corning) for 24 hours. 5-Fluorodeoxyuridine (FUdR, Sigma) was added at $3 \times 10^{-6}$ M to increase $^{125}$IUdR uptake. At the end of the labeling period the monolayer was detached by 0.25% trypsin-EDTA (Gibco) treatment. Ten thousand labeled tumor cells mixed with monocytes at different ratios, in a total volume of 0.24 ml complete medium per well and containing samples to be tested were planted in 96-well flat-bottom plates. After 72 hour incubation, the plates were centrifuged and 0.1 ml supernatant from each well was harvested and counted in a gamma counter. The total radioactivity incorporated into tumor cells was determined by treatment of the tumor cells with 1% NaDodSO$_4$. Spontaneous release of radioactivity was determined from the supernatant of tumor cells cultured in medium without monocytes. Cytotoxicity (%$^{125}$IUdR release) was calculated from the mean cpm of triplicate samples by the following formula:

Cytotoxicity (%$^{125}$IUdR release) = $\dfrac{\text{Experimental } - \text{ spontaneous release}}{\text{Total } - \text{ spontaneous release}}$ MAF control was prepared by incubation of PBM at $5 \times 10^6$ cells/ml in RPMI-1640 medium containing 10% FBS and 10 ug/ml phytohemagglutinin A (PHA, Wellcome Research Laboratories, Beckenham, Kent, England) for 24 hours at 37° C. After 3 washing the stimulated PBM were resuspended in the original volume of RPMI-1640 medium plus 10% FBS, and were further cultivated for 24 hours. The supernatant was used as MAF-containing lymphokine control (Mantovani, A. et al. (1980) *Int. J. Cancer* 25, 691). The supernatant of human leukocyte cultures induced with 12-O-tetradecanoylphorbol-13-acetate (TPA) and PHA (Yip et al., supra; Vilcek et al. supra) was also tested for MAF activity.

Preparation of immunoadsorbents. Ascitic fluid was produced in BALB/c mice which were injected intraperitoneally with 0.4 ml of Pristane (Aldrich Chem. Co., Milwaukee, Wisc.), and 4 days later inoculated with $2 \times 10^6$ hybridoma cells. Pooled ascitic fluids were centrifuged at $12,800 \times g$ for 3 minutes to remove cellular debris, and immunoglobulins in the supernatant were precipitated with ammonium sulfate (40% saturation). The precipitate was collected by centrifugation, redissolved in a small volume of water, and dialyzed overnight at 4° C. against 0.1 M NaHCO$_3$/0.5M NaCl, pH 8.3. About 37.5 mg of immunoglobulins was bound to 3 ml of CNBr-activated Sepharose 4B (Pharmacia) according to Cuatrecasas and Anfinsen (1971) *Methods Enzymol.* 22,345. The buffer used for coupling was 0.1 M NaHCO$_3$/0.5M NaCl, pH 8.3. The remaining active groups on the beads were inactivated by 1 M monoethanolamine (Fisher Scientific Co., Fair Lawn, N.J.) at pH 8.0. The excess unadsorbed proteins were washed away by the coupling buffer, followed by 0.1M acetate/0.5M NaCl, pH 4. The gel was reequilibrated in coupling buffer and stored in PBS containing 0.005% NaN$_3$ at 4° C.

NaDodSO$_4$/polyacrylamide gel electrophoresis. Electrophoresis was carried out in 12% acrylamide slab gels using the Laemmli procedure (Laemmli, U.K. (1970) *Nature* 227, 680). $^{125}$I-labeled natural IFN-gamma fraction with peak biological activity eluted from the monoclonal antibody affintiy column was applied to the gels. Upon completion of electrophoresis, the gel slab was cut into 1 mm slices, and the radioactivity of each slice was counted.

Results

Isolation and characterization of monoclonal antibodies. About 500 hybridoma cultures were obtained by fusion of SP2/0 cells with the splenocytes of a hyperimmunized mouse having a serum titer of 320 IFN-gamma neutralizing units per ml. Extensive screening by immunoprecipitation assay and SPRIA identified two hybridomas, B1 and B3, secreting substantial quantities of antibodies against human IFN-gamma. These two cell lines were subcloned several times by limiting dilution, and both monoclonal antibodies were identified as IgG1/kappa class by Ouchterlony's immunodiffusion test. Both antibodies showed dose-related binding to purified human natural IGFN-gamma as well as rIFN-gamma in both SPRIA and immunoprecipitation assays, with B3 having a higher affinity than B1 (FIGS. 1 and 2).

FIG. 1 illustrates the dose related binding observed with the solid phase immunoassay. Hybridomas were cultured in growth medium at approximately $3 \times 10^5$ cells/ml for 5 days, and the supernatants were diluted serially. Results are expressed as the radioactivity of second antibody adsorbed in vinyl wells in which B1 bound to rIFN-gamma (closed circles) or IFN-gamma (closed triangles), and B3 bound to rIFN-gamma (open circles) or IFN-gamma (open triangles). The specific activity of natural IFN-gamma and rIFN-gamma was $1-5 \times 10^5$ U/mg and $1 \times 10^6$ U/mg, respectively.

Figure 2:
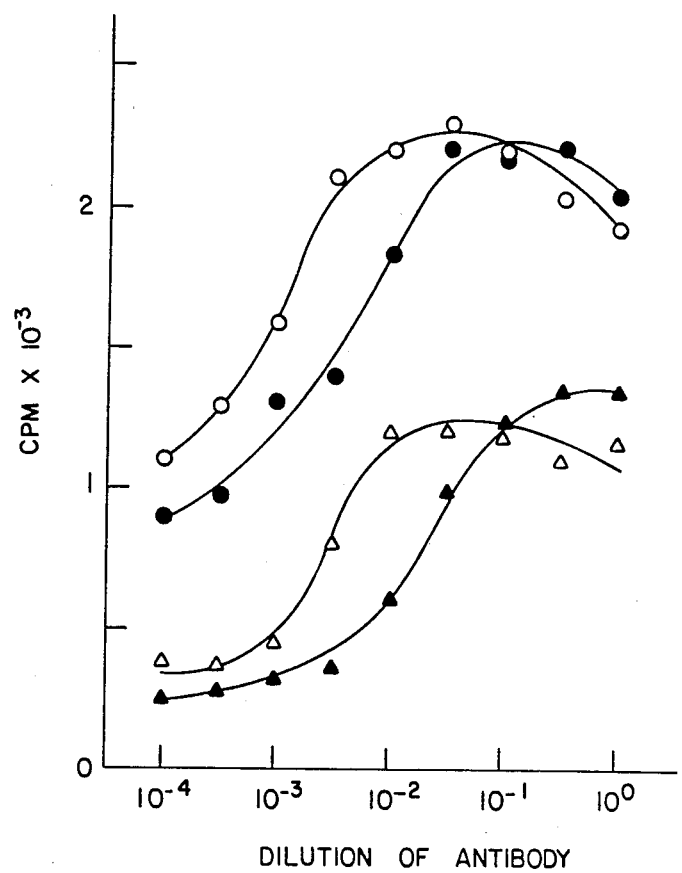
FIG. 2 illustrates the concentration related binding of monoclonal antibodies B1 and B3 to natural and recombinant huIFN-gamma in an immunoprecipitation assay.

Results of an immunoprecipitation assay are depicted in FIG. 2. Hybridomas were cultured in growth medium at approximately $3 \times 10^5$ cells/ml for 5 days, and the supernatants were diluted serially. Results are expressed as the radioactivity of immunoprecipitates formed by binding of B1 and $^{125}$I-rIFN-gamma (closed circles), B1 and $^{125}$I-IFN-gamma (closed triangles), B3 and $^{125}$I-rIFN-gamma (open circles) or B3 and $^{125}$I-IFN-gamma (open triangles). The specific activity of natural IFN-gamma and rIFN-gamma was $1-5\times10^5$ U/mg and $1\times10^6$ U/mg, respectively.

Marked binding activities of the antibodies in culture supernatants was regularly observed at $10^{-1}$ to $10^{-2}$ dilutions. The differences in the amounts of the antibodies bound to natural IFN-gamma and rIFN-gamma were apparently due to the higher specific activity of the latter preparation. Ascitic fluids, harvested about 10 days after inoculation of B1 or B3 hybridoma cells into BALB/c mice, showed significant binding activities at $10^{-6}$ dilution in the immunoprecipitation assay (results not shown).

Neutralization of antiviral activity of IFN-gamma by monoclonal antibody. Neutralization assays showed that the antiviral activities of both natural and recombinant IFN-gamma were completely neutralized by treatment with monoclonal antibody B3, but not B1, indicating that B3 and B1 recognized different epitopes on IFN-gamma molecules (Table 1).

TABLE I

Neutralization of IFN-gamma by monoclonal antibody

| Antibody[a] | IFN (units/ml) | | | |
|---|---|---|---|---|
| | IFN-alpha | IFN-beta | IFN-gamma | rIFN-gamma |
| None | 256 | 192 | 128 | 256 |
| B1 | ND | ND | 128 | 256 |
| B3 | 256 | 192 | 4 | 4 |

[a]The hybridoma B1 and B3 culture supernatants diluted 1:5 with medium, or the blank medium were incubated with various human IFN preparations for 1 hour at 37° C., and residual IFN activities were determined.

The culture supernatant and ascitic fluid of hybridoma B3 were found to contain approximately 1,000 and 50,000 neutralizing units/ml, respectively. Since B3 did not neutralize either IFN-alpha or IFN-beta, this monoclonal antibody appears to be specific for IFN-gamma.

The B3 antibody reacts only with the active form of huIFN-gamma. The results of a solid phase radioimmunoassay for B3 reactivity toward active and denatured IFN-gamma are shown in Table II. Radiolabeled B3 antibody bound and insolubilized active IFN-gamma but not to IFN-gamma denatured by acid (pH and heat treatment.

TABLE II

B3 Antibody Recognizes Active huIFN-gamma In Solid Phase Radioimmunoassay

| HuIFN-gamma | Radioactivity (cpm) bound to solid phase (mean ± SD) |
|---|---|
| Active IFN-gamma (500 U) | 241 ± 21 |
| Denatured IFN-gamma (500 U) | 51 ± 4 |
| None | 32 ± 4 |

Neutralization of macrophage activation. Several recent studies have shown that IFN-gamma-containing preparations can induce enhanced cytotoxicity of monocytes and macrophages for tumor cells. The data presented in Table III show that increased cytotoxicities of monocytes activated by natural or recombinant IFN-gamma at low concentrations (1 or 10 units/ml) were completely abolished by antibody B3 clearly indicating that IFN-gamma is the only molecule responsible for this activity in both IFN-gamma preparations.

TABLE III

Abrogation of MAF-like activity of pure IFN-gamma preparations by monoclonal antibody B3

| | Cytoxicity (% $^{125}$IUdR-release)[b] | | |
|---|---|---|---|
| | | Ratio of monocytes/HT-29 | |
| Sample[a] | No monocytes | 20 | 10 |
| Control medium | — | 9.6 | 4.2 |
| IFN-gamma | | | |
| 10 U/ml | 2.6 | 24.4 | 17.6 |
| 10 U/ml + B3 | 0.3 | 7.5 | 5.2 |
| 1 U/ml | 0.9 | 19.6 | 15.0 |
| 1 U/ml + B3 | −0.3 | 4.3 | 3.9 |
| rIFN-gamma | | | |
| 10 U/ml | 3.1 | 24.5 | 17.8 |
| 10 U/ml + B3 | 0.9 | 6.3 | 5.3 |
| 1 U/ml | 0.6 | 18.4 | 13.4 |
| 1 U/ml + B3 | 0.2 | 4.1 | 3.1 |

[a]Human purified IFN-gamma or rIFN-gamma were incubated with monoclonal antibody B3 or control medium for 1 hour at 37° C. prior to determination of MAF activities. The IFN titers based on antiviral activity were final.
[b]HT-29 cells were labeled with $^{125}$IUdR for 24 hours and cultured with (or without) human monocytes in the presence of the samples indicated for 72 hours. The radioactivities in culture supernatants were counted, and the cytotoxicities, expressed as % $^{125}$IUdR-release, were determined as described above.

Availability of a neutralizing monoclonal antibody also made it possible to examine the still unresolved question whether the lymphokine, termed macrophage activating factor (MAF), present in the supernatants of PBM stimulated with T cell mitogens, is different from IFN-gamma. The results of an experiment with two crude MAF-containing lymphokine preparations are shown in Table IV.

TABLE IV

Abolishment of MAF activities in mitogen-induced lymphocyte cultures by monoclonal antibody B3

| | IFN titer (units/ ml) | Cytoxicity (% $^{125}$IUdR-release)[b] at ratio of monocytes/HT-29 | |
|---|---|---|---|
| Sample[a] | | 20 | 10 |
| Control medium (CM) | | 10.2 | 5.9 |
| TPA/PHA supernatant + CM | 1,200 | 26.7 | 26.8 |
| TPA/PHA supernatant + B3 | 1 | 8.2 | 7.5 |
| PHA supernatant + CM | 5 | 23.6 | 22.5 |
| PHA supernatant + B3 | 1 | 4.5 | 4.1 |

[a]Supernatants of human lymphocyte cultures induced with TPA/PHA or PHA alone were incubated with B3 ascites or control medium for 1 hour at 37° C. Both MAF and IFN activities were then determined. IFN titers indicated were final.
[b]See Table III.

The supernatants of PBM induced with TPA and PHA or with PHA alone, contained both antiviral and MAF activities. In spite of the lower antiviral activity of the preparation produced with PHA alone, this preparation (which has been used as a standard MAF control) showed high MAF activity. These results are in agreement with our earlier findings that very low doses of IFN-gamma (in terms of antiviral units) are sufficient to produce near-maximal enhancement of monocyte cytotoxicity in this assay. When antiviral activity was neutralized with B3 ascites, MAF activity was also abrogated in both preparations. The fact that both activities were coincidently abolished by B3 ascites indicates that MAF activity in these preparations is due entirely to IFN-gamma.

Figure 3:
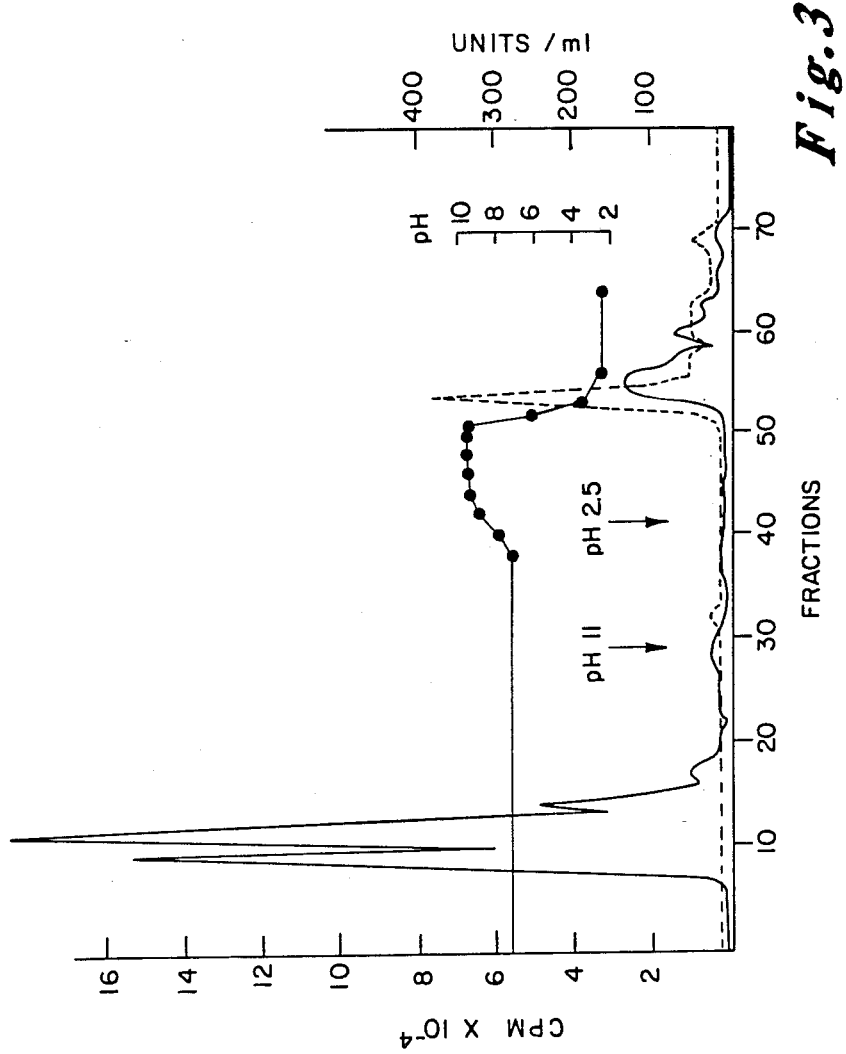
FIG. 3 illustrates an elution profile of $^{125}$I- huIFN-gamma from a B1-Sepharose immunoadsorbent column.

Affinity chromatography. In an attempt to use the monoclonal antibodies for IFN-gamma purification by affinity chromatography, immunoadsorbent Sepharose was prepared with ascitic fluid B1 (hereafter, B1-Sepharose). A preparation of $^{125}$I-labeled IFN-gamma purified by a four-step protocol containing about 1,500 units and $1\times 10^{-6}$ cpm in a total volume of 0.5 ml was loaded onto 0.15 ml of B1-Sepharose. The B1-Sepharose was washed with 1 ml of PBS/1M NaCl, and unbound fractions (Fr. 6-29) were collected. Although the unbound fractions represented 78% of total radioactivity, no detectable IFN-gamma activity was obtained (Table V). Bound material was eluted with 0.15M NaCl/NH$_4$OH, pH 11, followed by 0.1M citrate-phosphate buffer, pH 2.5 (FIG. 3). Fifty μl fractions were collected directly into 100 μl of Eagle's minimal essential medium with 5% FBS. FIG. 3 shows the elution profile of antiviral activity ( - - - - - ), radioactivity (————). A profile of pH is also shown ( -•-•- ).

In order to minimize inactivation of IFN-gamma, the resulting fractions were immediately adjusted to neutrality by dilution in medium. A major peak of IFN-gamma activity was eluted at about pH 3.5 (Fr. 52-56) containing 51% of total original IFN-gamma activity and 8% of total radioactivity. As the elution buffer reached pH 2.5, an additional 30% of IFN-gamma activity and 8% of radioactivity were recovered (Fr. 57-70). Since the IFN-gamma preparation used for iodination had been purified to within 80-90% of homogeneity, the fact that 81% cumulative IFN biological activity was recovered in Fr. 52-70 containing only 16% of total radioactivity strongly suggests that monoclonal antibody B1 may only recognize and bind to active IFN-gamma. The unbound fractions (Fr. 6-29) probably contained the bulk of inactivated IFN-gamma, formed during the process of purification and iodination together with contaminating protein.

TABLE V

Affinity chromatography of $^{125}$I-IFN-gamma with monoclonal antibody B3-conjugated Sepharose

| Fraction (No.)[a] | IFN-gamma activity | | IFN-gamma radioactivity | |
|---|---|---|---|---|
| | Total units | % | Total cpm × 10$^{-3}$ | % |
| Starting preparation | 1,512 | 100 | 1,007 | 100 |
| Unbound (6-29) | 0 | 0 | 781 | 78 |
| pH 3.5 elution (52-56) | 768 | 51 | 81 | 8 |
| pH 2.5 elution (57-70) | 455 | 30 | 83 | 8 |

[a]Fifty ul fractions were collected directly into 100 ul medium plus 5% FBS. Each fraction was determined for both antiviral activity and radioactivity.

Figure 4:
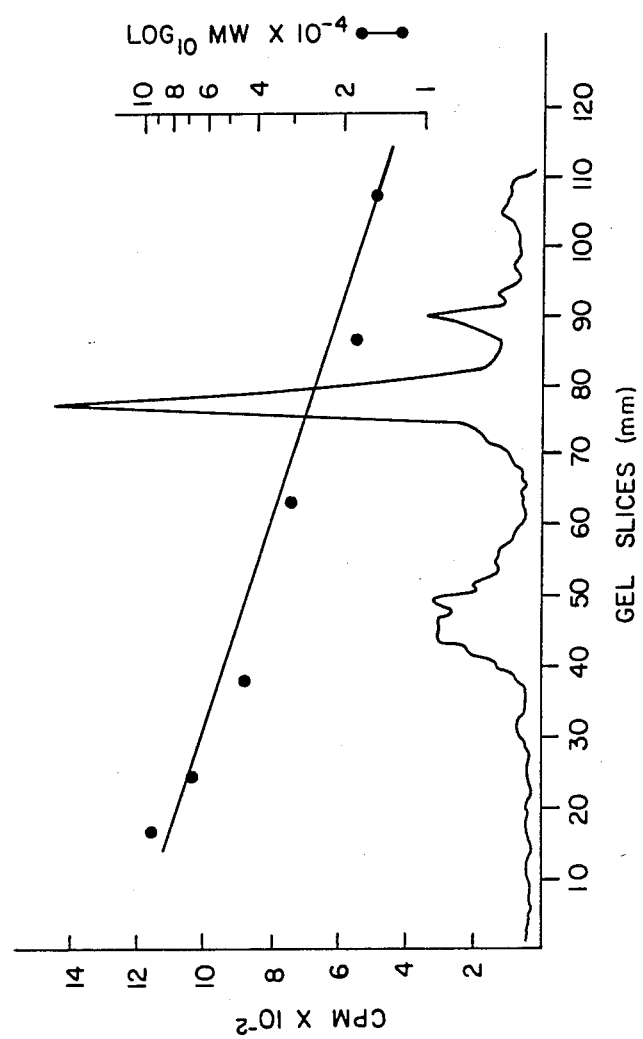
FIG. 4 illustrates the electrophoretic migration pattern on SDS-PAGE of an huIFN-gamma fraction from affinity chromatography with the antibody B3 having peak interferon activity.

An aliquot of an eluted fraction with peak antiviral activity was applied to NaDodSO$_4$/polyacrylamide gel electrophoresis (SDS-PAGE) to determine whether any subspecies of IFN-gamma was preferentially recognized by monoclonal antibody B1. An aliquot of Fr.55 containing $1.4\times 10^{-4}$ cpm in 100 μl was applied to 12% SDS-PAGE slab gels. Upon completion of electrophoresis the gel slab was cut into 1 mm slices and each slice was counted in a gamma counter. Three major peaks of radioactivity with m.w. of 45,000, 25,000 and 20,000 were observed upon completion of electrophoresis (FIG. 4). These peaks correspond to the SDS-PAGE profile of human IFN-gamma recognized on the basis of biological activity and radioactivity. It was concluded that the 45,000 m.w. form represents undissociated dimers and the two smaller bands represent monomeric forms differing in the amount of carbohydrate. The ratios of these three IFN-gamma species in the eluted fraction were similar to the ratios found in purified IFN-gamma.

EXAMPLE 2

Immunoassay for biologically active huIFN-gamma.

Preparation of IFN-gamma standards: HuIFN-gamma was obtained from the culture medium of lymphocyte-rich plateletpheresis residue induced with phytohemagglutinin A and 12-O-tetradecanoylphorbol-13-acetate. HuIFN-gamma was partially purified by a four step protocol to $4\times 10^4$ units/mg by the procedure of Yip, Y.K. et al., supra. IFN-gamma standards used for the immunoradiometric assay (IRMA) were prepared from this stock solution with various diluents. N.I.H. IFN-gamma standard was obtained from Research Resources Branch, NIAID, Bethesda, MD. Purified recombinant E. coli-derived human IFN-gamma was provided by Genentech, Inc., South San Francisco, Calif.

Purification of B1 and B3 monoclonal antibodies. 15-20 ml ascitic fluids of mice bearing the hybridomas secreting B1 and B3 antibodies were added 1/10 volume of Tris buffer (1.0 M, pH 8.0), filtered through glass wool, passed through a column packed with 15 ml protein A-Sepharose 4B, and eluted with Tris buffer (0.1 M, pH 8.0). The two antibodies, both of which are IgG1, were retarded by the column and hence were separated from albumin, IgM, and immunoglobulins of other subclasses. The fractions contaminated with albumin and IgM were further purified by concentrating them and by passing them through the protein A column again. HPLC analysis indicated that the B1 and B3 antibody preparations were at least 95% IgG1.

Preparation of B1 antibody-coated polystyrene beads. Polystyrene balls, ¼ inch diameter (Precision Plastic Balls Co., Chicago, Ill.) were washed with ethanol and phosphate buffered saline (pH 7.4). The beads were coated with B1 antibody by a procedure similar to that described by Ziola et al. See Ziola et al. (1977) J. Immunol. Meth. 17, 309. Briefly, 1000 beads were incubated with shaking in 150 ml PBS (pH 7.4) containing 5.0 mg B1 antibody at room temperature for 16 hours. The beads were then washed with PBS three times and then incubated with 150 ml PBS containing 1% bovine serum albumin (BSA) at 37° C. for six hours. They were then washed with PBS twice and incubated with 150 ml stabilizer solution (polyvinylpyrrolidone, 4% w/v; glycerol, 10%, w/v aqueous solution) at room temperature for 30 minutes. The stabilizer solution was removed by centrifugation and the dried beads were stored in capped tubes at 4° C.

Preparation of $^{125}$I-B3 antibody tracer. B3 antibody was labeled with $^{125}$I by reacting with Na$^{125}$I using Chloramine T method of Hunter and Greenwood, supra. $^{125}$I-B3 has a specific radioactivity of 12-14 uCi/umole. It was diluted with PBS containing 0.5% BSA and 1% normal BALB/c mouse serum to 100,000 cpm/200 μl upon use.

Immunoradiometric assay for IFN-gamma. Assay standards using partially purified IFN-gamma were prepared using either PBS containing 0.2% BSA or pooled normal human serum as dilutants. The B1 antibody coated polystyrene beads (used as the solid phase immunoadsorbent for human IFN-gamma) were placed into wells of assay trays. 200 μl of standards were pipetted into the wells. The trays were shaken gently at room temperature for two hours. The beads were then washed with water. 200 μl of tracer solution (200 μl) containing 100,000 cpm $^{125}$I-B3 antibody was added, and the mixture was incubated at room temperature for three hours with shaking. After washing, the beads were counted for $^{125}I$ in a gamma-scintillation counter.

Figure 5:
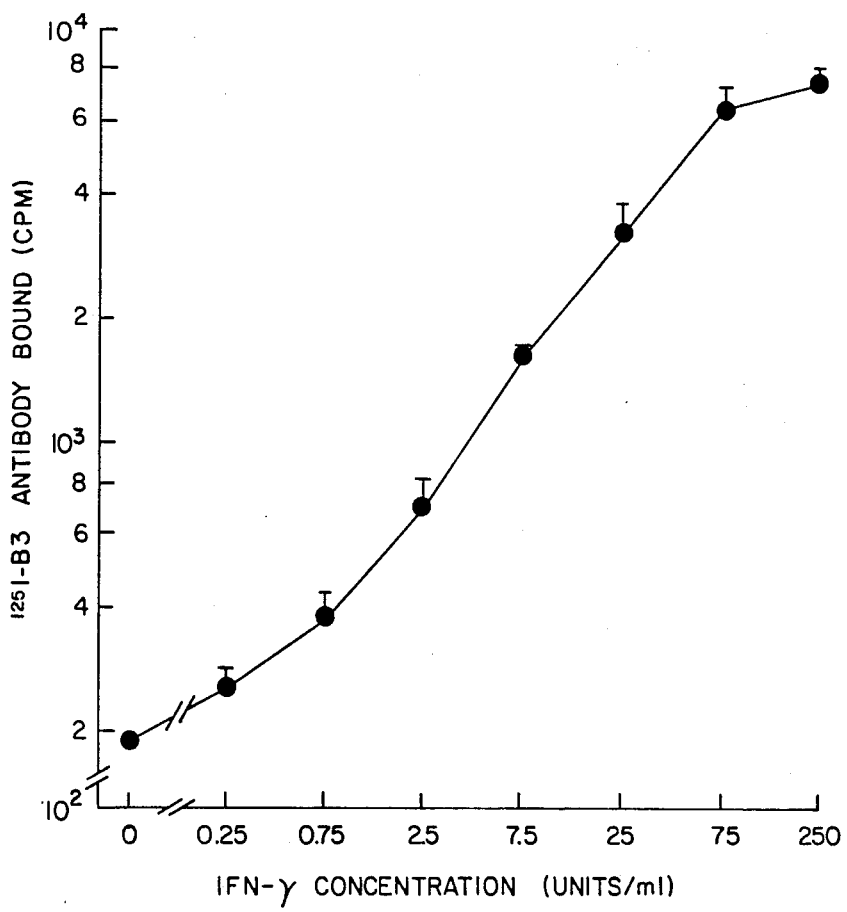
FIG. 5 illustrates the results of a forward sandwich immunoradiometric assay of huIFN-gamma using B1 antibody-coated polystyrene beads and $^{125}$I-labeled B3 antibody tracer.
Figure 6:
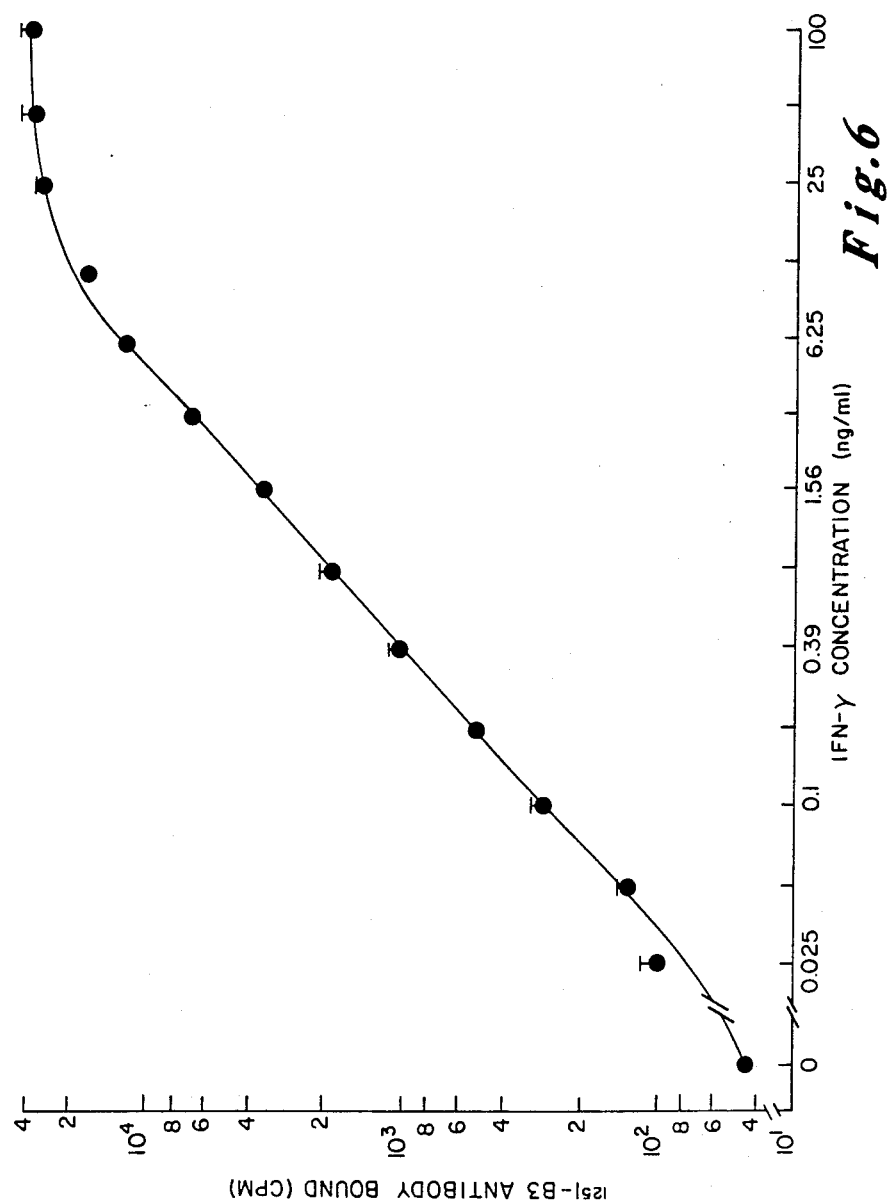
FIG. 6 illustrates the results of a sandwich immunoradiometric assay of recombinant E. coli-derived huIFN-gamma.

Results. Most of the procedure of the IRMA was established by using partially purified IFN-gamma from activated lymphocyte cultures. The IFN-gamma concentration was determined in a biological assay with a NIH standard as a reference. In final form, the forward sandwich solid phase IRMA comprises 2 steps and takes about 5–6 hours to run. Longer incubation time does not give better results. The background of this IRMA is 100–200 cpm (using 100,000 cpm tracer input). The sensitivity at the lower limit of the assay is about 200 cpm per 0.1 unit/ml of IFN-gamma, i.e. 0.1 unit/ml of IFN-gamma would give a signal twice of background (FIG. 5). The IRMA is reproducible, because standard deviations are, on average, within 10% of the mean. The sensitivity of the IRMA was also examined with purified recombinant *E. coli*-derived human IFN-gamma and found to be about 0.02 ng/ml. See FIG. 6.

Figure 7:
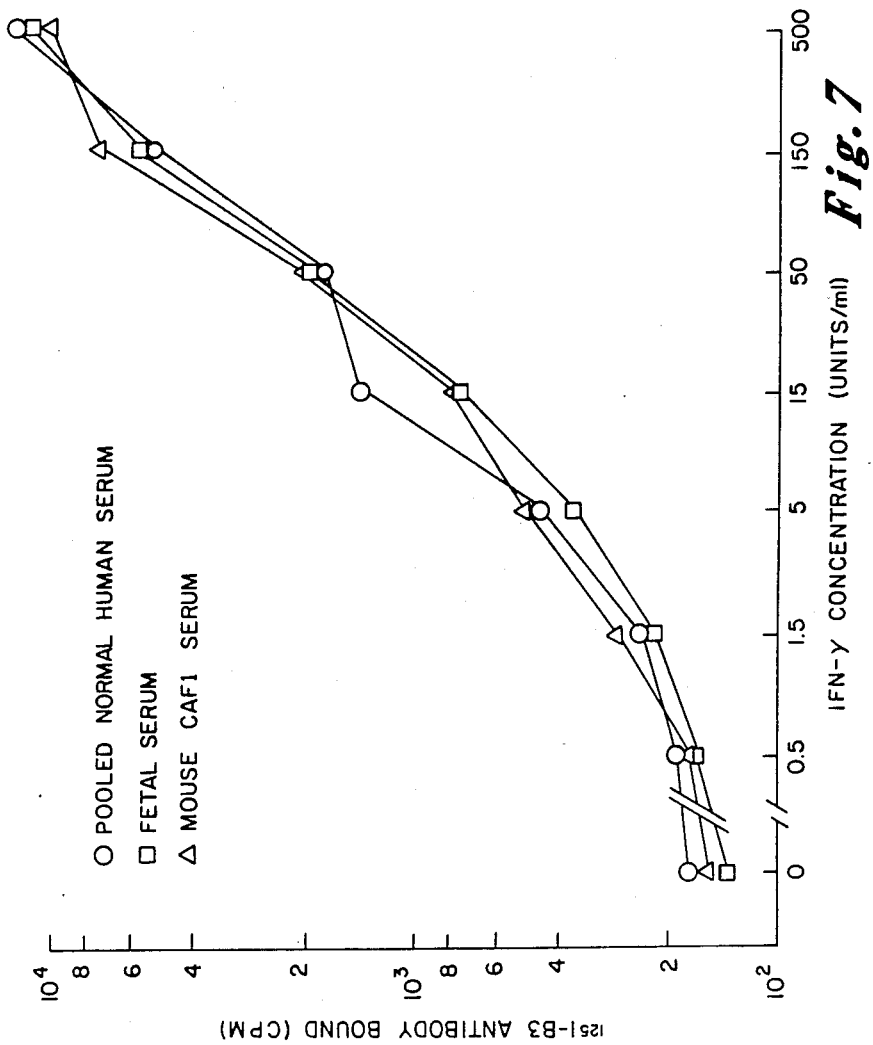
FIG. 7 illustrates results of a sandwich immunoradiometric assay of huIFN-gamma in human, fetal calf and mouse sera.
Figure 8:
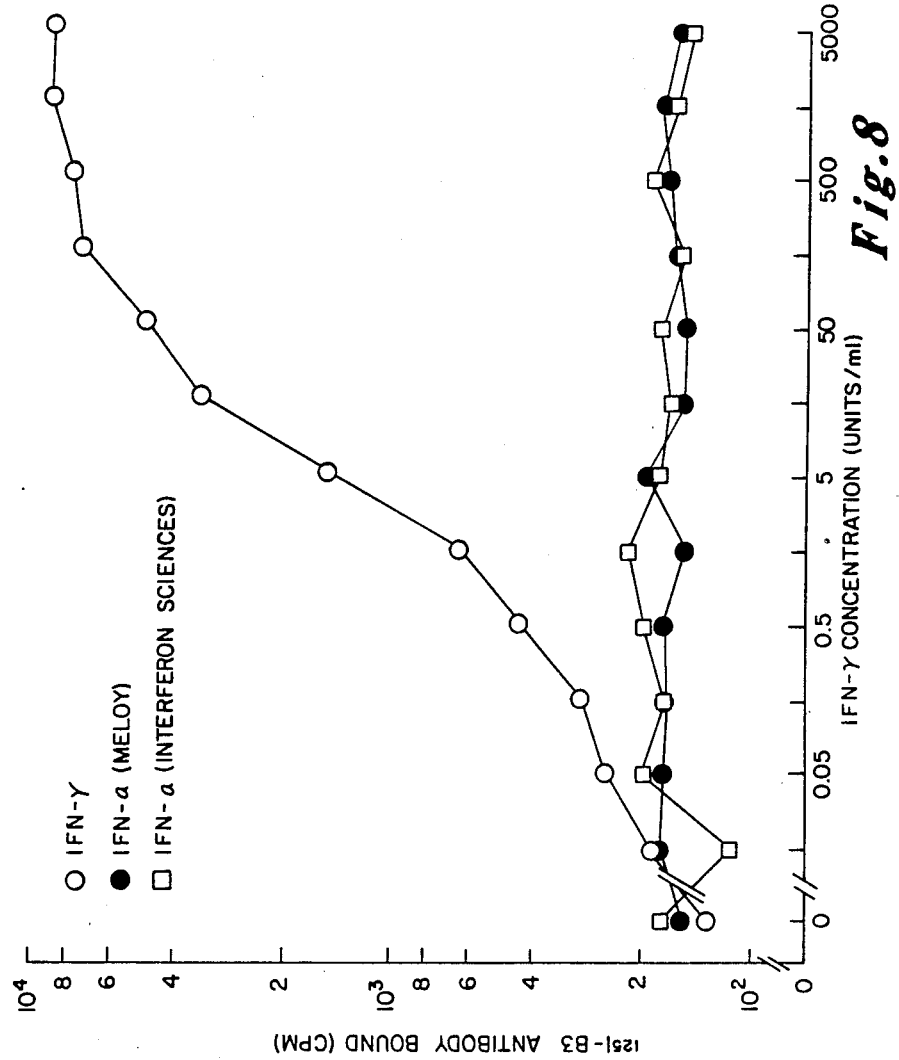
FIG. 8 illustrates that the B1–B3 sandwich immunoradiometric assay is interferon type specific.

Pooled human, fetal calf, or mouse sera as diluent did not increase the background or decrease the signal of IFN-gamma standards (FIG. 7). These results indicate that the assay is specific for human IFN-gamma and that there are no other substances in human serum cross-reactive with the two antibodies. They also indicate that the IFN-gamma levels in normal serum are below 0.1 unit/ml, the sensitivity limit of the assay. Unlike the viral cytopathic assays for interferons, the present immunochemical assay detects only IFN-gamma and not IFN-alpha (leukocyte interferon). At concentrations as high as 4000 units/ml, purified human IFN-alpha obtained from two commercial sources was completely negative (FIG. 8). IFN-beta (fibroblast interferon) has not been tested in this assay. In biological assays, however, the B3 antibody did not neutralize IFN-beta.

Figure 9:
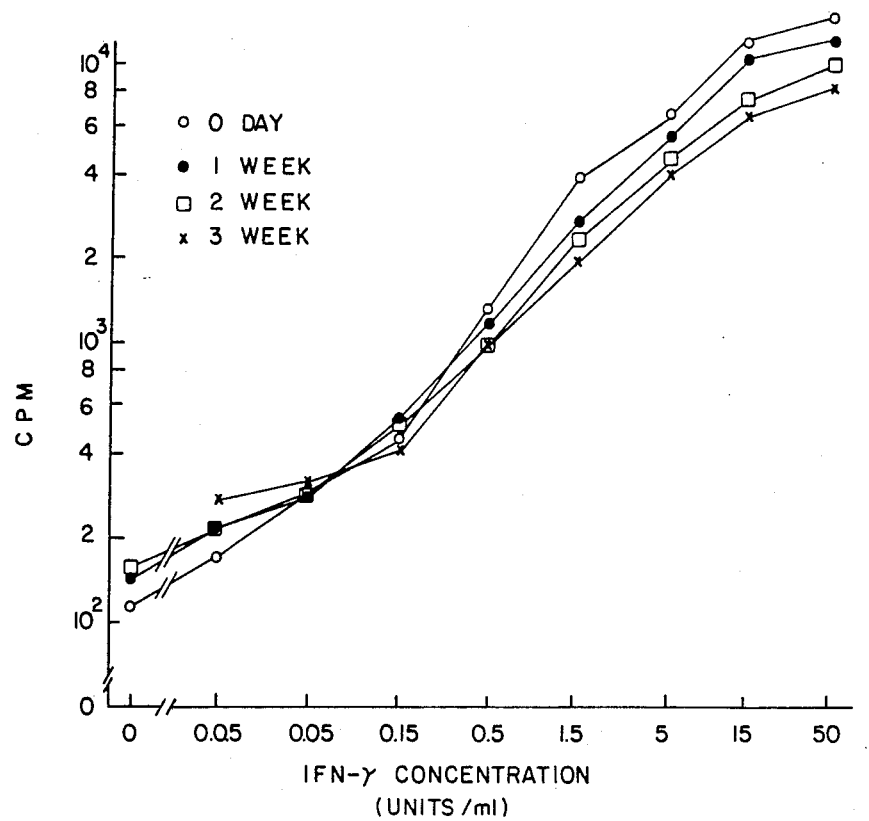
FIG. 9 illustrates the results of a B1–B3 sandwich immunoradiometric assay for huIFN-gamma performed after all kit components were stored at 4° C. for various periods of time.
Figure 10:
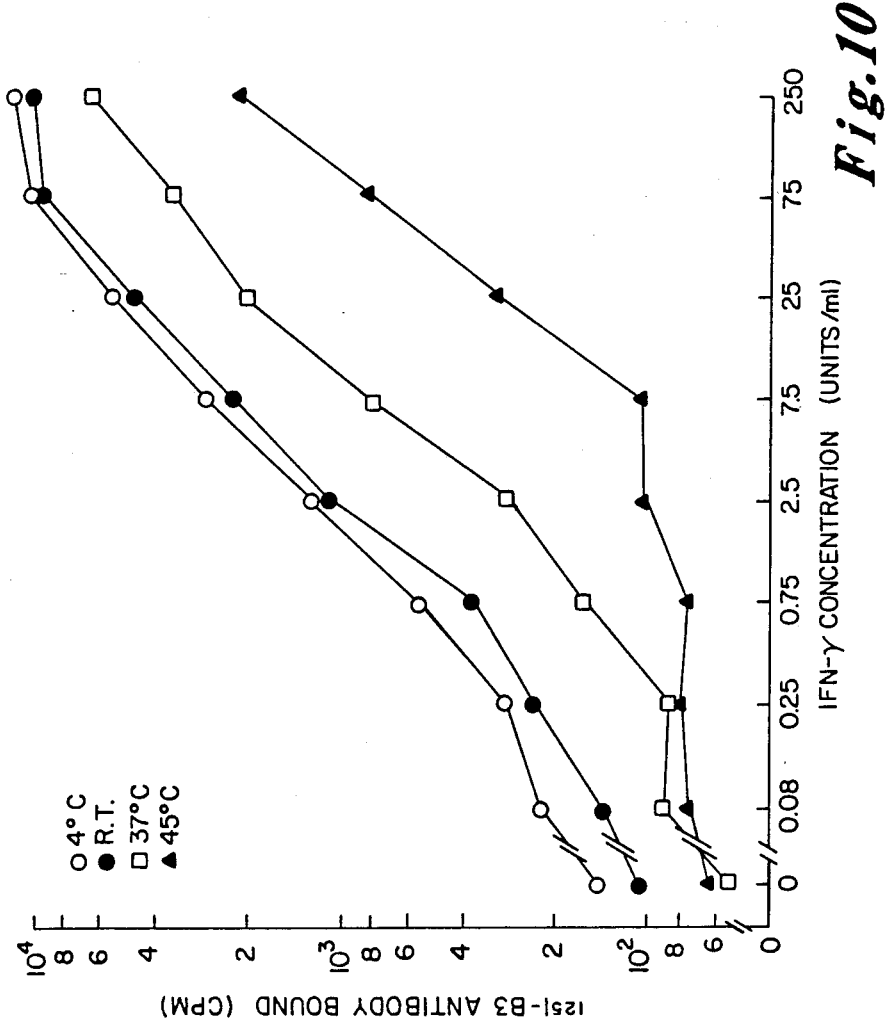
FIG. 10 illustrates the results of a B1–B3 antibody sandwich immunoradiometric assay for huIFN-gamma after all kit components were stored at various temperatures for one week.
Figure 11:
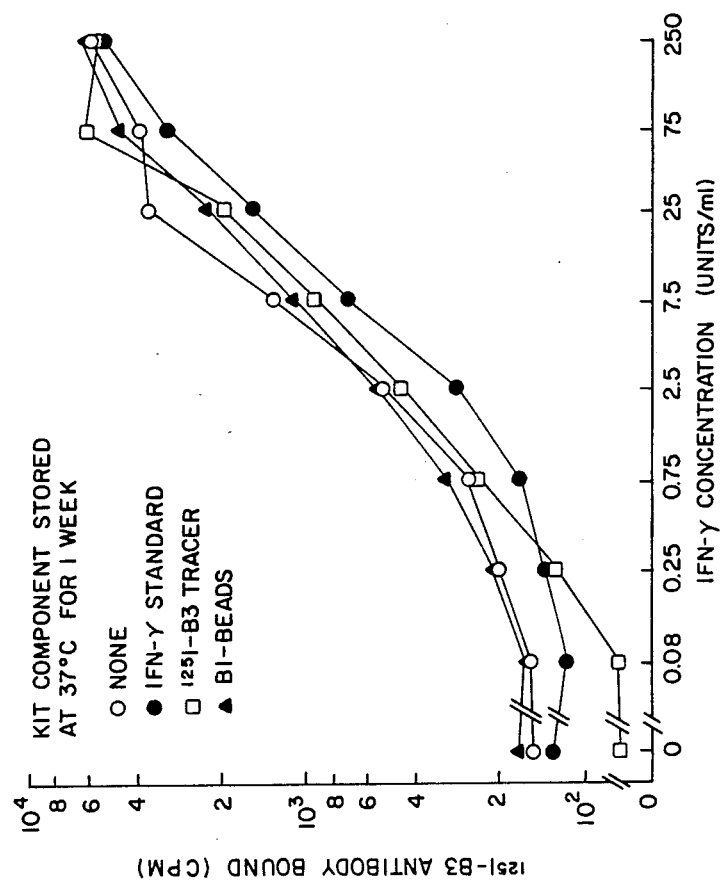
FIG. 11 illustrates the results of a B1–B3 antibody sandwich immunoradiometric assay for huIFN-gamma after one of the kit components was stored at 37° C. for one week.
Figure 12:
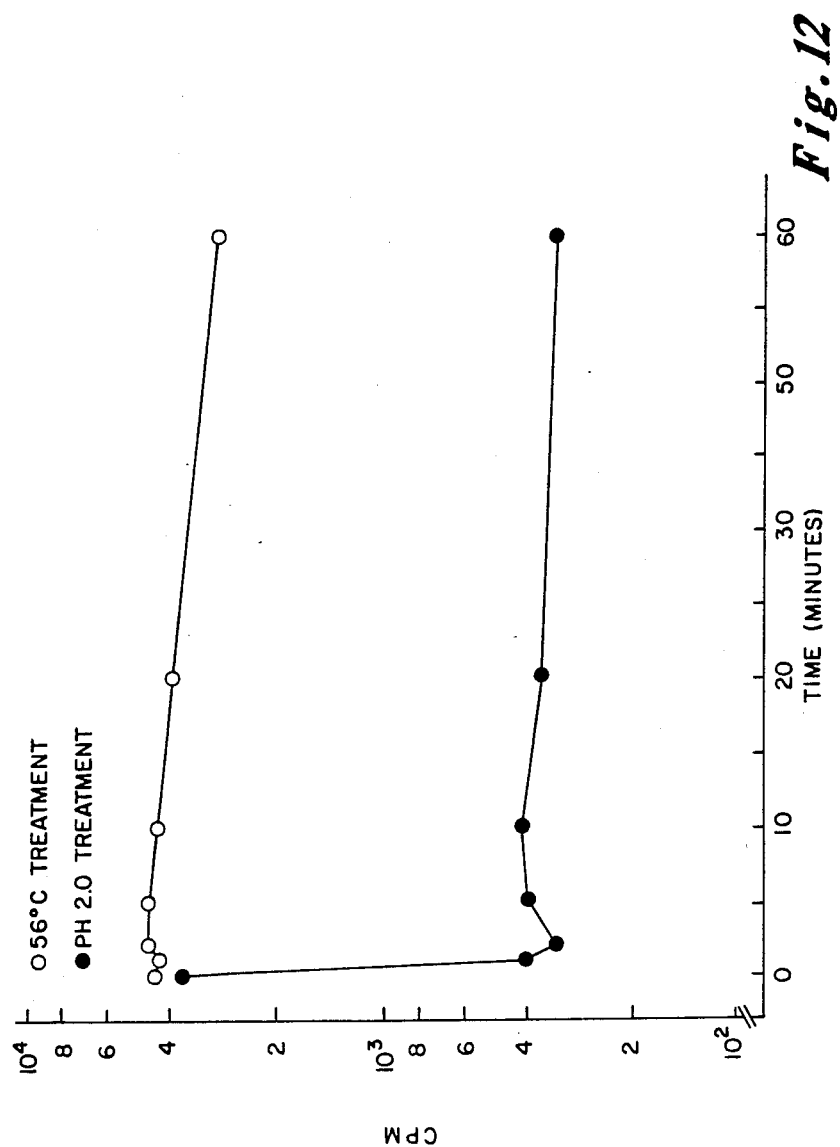
FIG. 12 illustrates results of a B1–B3 antibody sandwich immunoradiometric assay for chemically and heat inactivated huIFN-gamma.

The B1 antibody-coated immunoadsorbent beads, the $^{125}I$-B3 tracer, and the IFN-gamma standard were tested for stability after they were prepared. When the kits were stored at 4° C, they gave identical sensitivity for eight weeks although the signal intensity decreased somewhat due to decay of $^{125}I$ in the B3 tracer. (FIG. 9). At 37° C. or 45° C., the assay kits lost significant amounts of sensitivity after one week of storage (FIG. 10). When the individual components were examined for the instability at elevated temperatures, gamma-interferon standard was found to be the component that was not stable (FIG. 11). Reflecting that B3 antibody reacts only with biologically active and not denatured forms of IFN-gamma, the IRMA also detects only the active IFN-gamma. After the interferon was exposed to pH 2 or 56° C., it lost some reactivity in the IRMA (FIG. 12).

Industrial Applicability

The immunoassays described provide rapid, highly sensitive, inexpensive and reproducible methods for detection and quantification of biologically active natural or recombinant huIFN-gamma. The assays provide a substitute for existing bioassays for IFN-gamma which are more time-consuming and variable and much less sensitive and specific. Because of the stability of the reagents employed in the assays of this invention, they may be provided conveniently in kits.

The assays may be employed by hospitals or clinical laboratories to determine levels of huIFN-gamma in serum, plasma or other biological fluids of patients. The assays may also be used to monitor the ability of a patient's lymphocytes to produce IFN-gamma after appropriate stimulation outside the body. In addition, the assays may be used to monitor the production of biologically active huIFN-gamma by cultured mammalian cells or by genetically engineered microorganisms.

The methods of purifying huIFN-gamma described herein may be used to obtain purified, biologically active huIFN-gamma from tissue or cell culture media.

Because recently accumulated evidence suggests strongly that IFN-gamma is identical to macrophage activation factor, the assays of the invention also provide means for detecting and quantifying MAF activity, when this aspect of the activity of IFN-gamma is of concern.

Equivalents

Those skilled in the art will recognize, or be able to ascertain, by no more than routine experimentation, many equivalents of the specific embodiments of the invention described herein. Such equivalents are intended to be encompassed by the following claims.

We claim:

1. An assay for biologically active natural or recombinant huIFN-gamma in a liquid sample, comprising the steps of:
    a. forming an incubation mixture of the liquid sample and a solid phase immunoadsorbent containing either monoclonal anti-huIFN-gamma antibody B1 (ATCC accession number 40096) or B3 (ATCC accession number 40097);
    b. incubating the incubation mixture under conditions and for a period of time sufficient for huIFN-gamma in the liquid sample to bind to the immunoadsorbent;
    c. thereafter separating the immunoadsorbent from the liquid sample;
    d. forming an incubation mixture of the immunoadsorbent and soluble labeled monoclonal anti-huIFN-gamma antibody B1 or B3;
    e. incubating the mixture under conditions and for a period of time sufficient for the labeled antibody to bind any huIFN-gamma bound to the immunoadsorbent;
    f. separating the solid phase immunoadsorbent from unbound, labeled anti-huIFN-gamma antibody;
    g. detecting the amount of labeled monoclonal antibody bound to the immunoadsorbent or the amount of unbound, labeled antibody; and
    h. relating the amount of bound labeled monoclonal antibody or unbound labeled antibody detected to a predetermined quantitative relationship between the amount of labeled antibody and the amount of biologically active huIFN-gamma to determine the amount of biologically active huIFN-gamma in the liquid sample.

2. A method of claim 1 wherein the solid phase immunoadsorbent contains monoclonal antibody B1 and the labeled monoclonal antibody is monoclonal antibody B3.

3. An immunoassay for biologically active huIFN-gamma in a liquid sample, comprising the steps of:
    a. forming an incubation mixture of the liquid sample and soluble labeled monoclonal anti-huIFN-gamma antibody B1 (ATCC accessing number 40096) or B3 (ATCC accession number 40097);
    b. incubating the incubation mixture under conditions and for a period of time sufficient for huIFN-gamma in the liquid sample to bind the labeled, soluble monoclonal antibody;

c. contacting a solid phase immunoadsorbent containing either monoclonal anti-huIFN-gamma antibody B1 or B3 with the incubation mixture under conditions and for a period of time sufficient for huIFN-gamma bound to the labeled, soluble monoclonal antibody to bind the immunoadsorbent;

d. separating the solid phase immunoadsorbent from the incubation mixture;

e. detecting the amount of labeled monoclonal antibody bound to the solid phase immunoadsorbent or the amount of unbound labeled antibody; and f. relating the amount of labeled monoclonal antibody detected to a predetermined quantitative relationship between the amount of labeled antibody and amount of biologically active huIFN-gamma to determine the amount of biologically active huIFN-gamma in the liquid sample.

4. A method of claim 3 wherein the labeled monoclonal antibody is monoclonal antibody B3 and the solid phase immunoadsorbent contains monoclonal antibody B1.

5. An immunoassay for biologically active huIFN-gamma in a liquid sample, comprising the steps of:
 a. forming an incubation mixture of
   i. liquid sample;
   ii. a solid phase immunoadsorbent containing immobilized monoclonal anti-huIFN-gamma antibody B1 (ATCC accession number 40096) or B3 (ATCC accession number 40097); and
   iii. labeled soluble monoclonal anti-huIFN-gamma antibody B1 or B3;
 b. incubating said mixture under conditions and for a period of time sufficient for huIFN-gamma in the liquid sample to complex with the immobilized monoclonal antibody and the labeled, soluble, monoclonal antibody;
 c. thereafter separating said solid phase immunoadsorbent from the incubation mixture;
 d. detecting the amount of labeled monoclonal antibody bound to said solid phase immunoadsorbent or the amount of unbound labeled antibody; and
 e. relating the amount of labeled monoclonal antibody detected to a predetermined quantitative relationship between the amount of labeled antibody and the amount of huIFN-gamma to determine the amount of biologically active huIFN-gamma in the liquid samples.

6. A method of claim 5 wherein the solid phase immunoadsorbent comprises the monoclonal antibody B1 and the labeled antibody is monoclonal antibody B3.

7. A forward sandwich immunoradiometric assay for biologically active huIFN-gamma in a liquid sample comprising the steps of:
 a. forming an incubation mixture of the liquid sample and solid phase immunoadsorbent comprising polystyrene beads with monoclonal antibody B1 (ATCC accession number 40096) conjugated thereto;
 b. incubating the mixture for about 2 hours at room temperature;
 c. thereafter separating the immunoadsorbent from the liquid sample;
 d. forming an incubation mixture of the immunoadsorbent and soluble $^{125}$I-labeled monoclonal antibody B3 (ATCC accession number 40097);
 e. incubating the mixture for about 3 hours at room temperature;
 f. separating the immunoadsorbent from unbound $^{125}$I-labeled monoclonal antibody B3;
 g. detecting the amount of labeled antibody bound to the immunoadsorbent; and
 h. relating the amount of bound $^{125}$I-labeled monoclonal antibody B3 to a predetermined quantitative relationship between the amount of $^{125}$I-labeled monoclonal antibody B3 and the amount of biologically active huIFN-gamma to determine the amount of biologically active huIFN-gamma in the liquid sample.

8. In an immunoassay for a lymphokine selected from the group consisting of huIFN-gamma or MAF, the improvement of using monoclonal anti-huIFN-gamma antibody B1 (ATCC accession number 40096) or B3 (ATCC accession number 40097).

9. An assay kit for biologically active huIFN-gamma in a liquid sample, including:
 a. an immunoadsorbent containing monoclonal anti-huIFN-gamma antibody B1 (ATCC accession number 40096) or B3 (ATCC accession number 40097); and
 b. labeled monoclonal anti-huIFN-gamma antibody B1 or B3.

10. An assay kit of claim 9 further including:
 c. a huIFN-gamma standard.

11. An assay kit for biologically active huIFN-gamma in a liquid sample, including:
 a. an immunoadsorbent comprising polystyrene beads with monoclonal antibody B1 (ATCC accession number 40096 affixed thereto;
 b. $^{125}$I-labeled monoclonal antibody B3 (ATCC accession number 40097 and
 c. a huIFN-gamma standard.

12. A method of isolating biologically active huIFN-gamma from a liquid, comprising the steps of:
 a. contacting the liquid with an immuno-adsorbent containing monoclonal anti-huIFN-gamma antibody B1 (ATCC accession number 40096) or B3 (ATCC accession number 40097), under conditions which permit adsorption of the huIFN-gamma to the immunoadsrobent;
 b. separating the liquid and the immunoadsorbent; and
 c. recovering the biologically active huIFN-gamma from the immunoadsorbent.

13. An immunoadsorbent comprising a solid phase to which is attached monoclonal anti-huIFN-gamma antibody B1 (ATCC accession number 40096) or B3 (ATCC accession number 40097).

14. Monoclonal anti-huIFN-gamma antibody B1, ATCC accession number 40096.

15. Monoclonal anti-huIFN-gamma antibody B3, ATCC accession number 40097.

* * * * *